United States Patent [19]

Tanaka et al.

[11] Patent Number: 5,344,985
[45] Date of Patent: Sep. 6, 1994

[54] ALDEHYDE INTERMEDIATES FOR THE PREPARATION OF PYRENYLAMINE DERIVATIVES HAVING UNSATURATED BOND

[75] Inventors: Chiaki Tanaka, Shizuoka; Masaomi Sasaki, Susono; Tamotsu Aruga, Mishima; Tomoyuki Shimada, Shizuoka; Hiroshi Adachi, Numazu, all of Japan

[73] Assignee: Ricoh Company, Ltd., Tokyo, Japan

[21] Appl. No.: 996,080

[22] Filed: Dec. 23, 1992

[30] Foreign Application Priority Data

| Dec. 28, 1991 | [JP] | Japan | 3-360363 |
| Apr. 15, 1992 | [JP] | Japan | 4-121326 |
| Jun. 8, 1992 | [JP] | Japan | 4-173818 |
| Jul. 17, 1992 | [JP] | Japan | 4-213528 |
| Jul. 17, 1992 | [JP] | Japan | 4-213529 |

[51] Int. Cl.$^5$ ............................................. C07C 223/06
[52] U.S. Cl. ................................. 564/426; 558/418; 564/307; 564/308
[58] Field of Search ............... 558/418; 564/307, 308, 564/426

[56] References Cited

U.S. PATENT DOCUMENTS 2,185,661  1/1940  Corell et al. ..................... 564/426

FOREIGN PATENT DOCUMENTS 4036264  2/1992  Japan .

*Primary Examiner*—Richard L. Raymond
*Attorney, Agent, or Firm*—Oblon, Spivak, McClelland, Maier & Neustadt

[57] ABSTRACT

A pyrenylamine derivative having an unsaturated bond of formula (I), which can be employed as an organic photoconductive material for use in electrophotography:

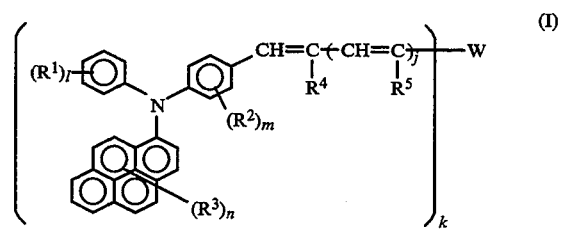

wherein $R^1$, $R^2$, $R^3$, $R^4$, $R^5$, W, l, m, n j and k are specifically defined the specification, an aldehyde compound of formula (II), which is an intermediate for preparing the pyrenylamine derivative:

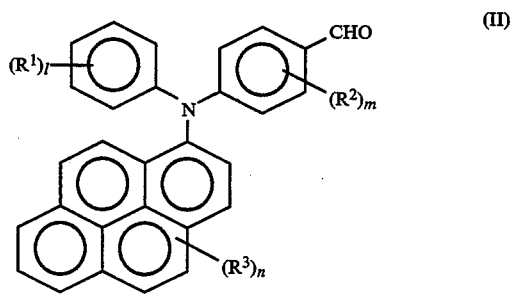

and methods of producing the pyrenylamine derivative and the aldehyde compound are disclosed.

9 Claims, 5 Drawing Sheets

ALDEHYDE INTERMEDIATES FOR THE PREPARATION OF PYRENYLAMINE DERIVATIVES HAVING UNSATURATED BOND

BACKGROUND OF THE INVENTION

1. Field of the Invention

The present invention relates to pyrenylamine derivatives having an unsaturated bond, which are useful as organic photoconductive materials for use in electrophotographic photoconductors and fluorescent whitening agents, aldehyde compounds serving as intermediates for producing the pyrenylamine derivatives, and methods for preparing the aldehyde compounds and the pyrenylamine derivatives.

2. Discussion of Background

Conventionally, many organic photoconductive materials for use in an electrophotographic process have been proposed. For example, there are known photoconductors comprising poly-N-vinylcarbazole or a triphenylamine compound as disclosed in U.S. Pat. No. 3,180,730; photoconductors comprising benzidine compounds as disclosed in U.S. Pat. No. 3,265,496, Japanese Patent Publication 39-11546, and Japanese Laid-Open Patent Application 53-27033; and photoconductors comprising stilbene compounds as disclosed in Japanese Laid-Open Patent Applications 58-198425, 58-198043, 58-189145, and 58-190953.

The above-mentioned electrophotographic process is one of an image forming processes, through which the surface of a photoconductor is charged in the dark by corona charges or the like. The charged photoconductor is exposed to a light image to selectively dissipate the electrical charges from the exposed areas, so that a latent electrostatic image is formed on the photoconductor. Furthermore, the thus formed latent electrostatic image is developed by a developer such as toner to a visible image.

Fundamental characteristics required for the photoconductor for use in such an electrophotographic process are: (1) chargeability to an appropriate potential in the dark, (2) minimum dissipation of electrical charge in the dark, and (3) quick dissipation of electrical charge when exposed to light.

However, the conventionally organic photoconductive materials have not satisfied the above-mentioned requirements (1) to (3) completely in practice.

On the other hand, inorganic materials such as selenium and zinc oxide are known as photoconductive materials for use in electrophotographic photoconductors. In particular, selenium photoconductors are widely used in practice. From the viewpoint of the recent electrophotographic process, in addition to various requirements for the electrophotographic photoconductors such as the above-mentioned fundamental characteristics, for instance, electrophotographic photoconductors have been required to be in the form of a belt with high flexibility. However, in the case of the selenium photoconductor, it is difficult to work them into the form of a belt.

To eliminate the shortcomings of the inorganic materials, various electrophotographic photoconductors employing organic materials have been proposed recently and some are put to practical use. Examples of the electrophotographic photoconductors employing organic materials are photoconductors comprising stilbene derivatives as disclosed in Japanese Laid-Open Patent Applications 58-198425 and 58-189145; and photoconductors comprising triarylamine derivatives as disclosed in Japanese Laid-Open Patent Application 58-65440. However, these photoconductors are still unsatisfactory for use in electrophotography.

SUMMARY OF THE INVENTION

It is therefore a first object of the present invention to provide novel aldehyde compounds serving as intermediates for producing novel pyrenylamine derivatives having an unsaturated bond, which are useful as photoconductive materials for use in the electrophotoconductive photoconductor and can satisfy all the fundamental characteristics required for electrophotographic photoconductor.

A second object of the present invention is to provide a method of preparing the above-mentioned novel aldehyde compounds.

A third object of the present invention is to provide the above-mentioned novel pyrenylamine derivatives having unsaturated bonds.

A fourth object of the present invention is to provide methods of preparing the above-mentioned novel pyrenylamine derivatives.

The first object of the present invention can be achieved by an aldehyde compound of formula (I):

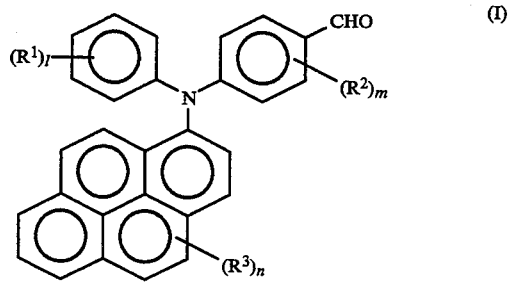

wherein $R^1$ and $R^2$ each represent hydrogen, a halogen atom, nitro group, cyano group, a dialkylamino group, an alkyl group having 1 to 10 carbon atoms, an alkoxyl group having 1 to 10 carbon atoms, or phenyl group; $R^3$ represents hydrogen or an alkyl group having 1 to 10 carbon atoms; l is an integer of 1 to 5; m is an integer of 1 to 4; n is an integer of 1 to 3; and when l, m or n is 2 or more, , $R^1$, $R^2$ and $R^3$ may be the same or different.

The second object of the present invention can be achieved by a method of preparing the aldehyde compound of formula (I) comprising the step of subjecting a diphenylaminopyrene compound of formula (II) to formylation:

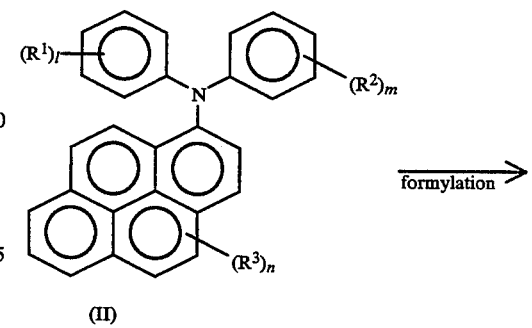

-continued

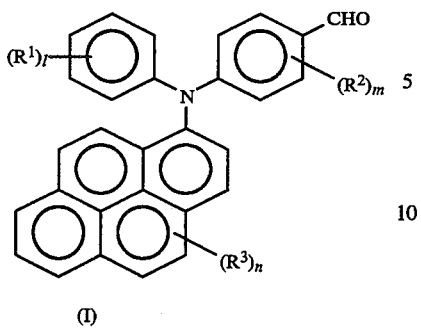

wherein $R^1$, $R^2$, $R^3$, l, m and n are the same as defined in formula (I).

The third object of the present invention can be achieved by a pyrenylamine derivative having an unsaturated bond of formula (III):

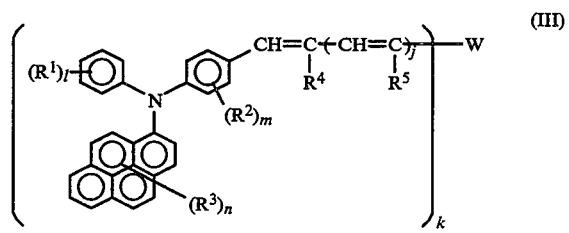

wherein $R^1$, $R^2$, $R^3$, l, m and n are the same as defined in formula (I); $R^4$ and $R^5$ each represent hydrogen, cyano group, formyl group, an alkoxylcarbonyl group, an alkyl group having 1 to 10 carbon atoms, an alkenyl group having 1 to 10 carbon atoms, or phenyl group; W represents hydrogen, an alkyl group having 1 to 10 carbon atoms, a phenylthio group, a bivalent group comprising a chain unsaturated hydrocarbon, a monovalent or bivalent carbocyclic aromatic group, or a monovalent or bivalent group comprising a heterocyclic ring; j is an integer of 0 to 2; k is an inter of 1 or 2; and when l, m or n is 2 or more, $R^1$, $R^2$, and $R^3$ may be the same or different.

The fourth object of the present invention can be achieved by a method of preparing the pyrenylamine derivative having an unsaturated bond of formula (III) comprising the step of allowing an aldehyde compound of formula (I) to react with a phosphorus compound of formula (IV) in accordance with the following reaction scheme:

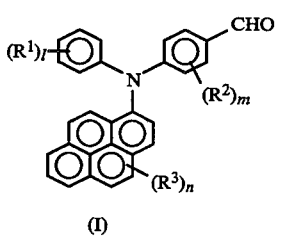

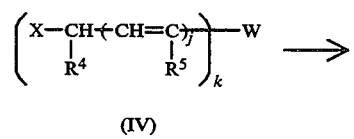

wherein $R^1$, $R^2$, $R^3$, l, m, and n are the same as defined in formula (I); $R^4$, $R^5$, W, j and k are the same as defined in formula (III); X in formula (IV) represents a phosphonium salt represented by $-P+(R^6)_3Y^-$, or a dialkylphosphite group represented by $-PO(OR^7)_2$, in which $R^6$ represents phenyl group or an alkyl group having 1 to 10 carbon atoms, Y represents a halogen atom, and $R^7$ represents an alkyl group having 1 to 10 carbon atoms., The fourth object of the present invention can also be achieved by a method of preparing the pyrenylamine derivative having an unsaturated bond of formula (III) comprising the step of allowing a secondary amine compound of formula (V) to react with a pyrene compound of formula (VI) in accordance with the following reaction scheme:

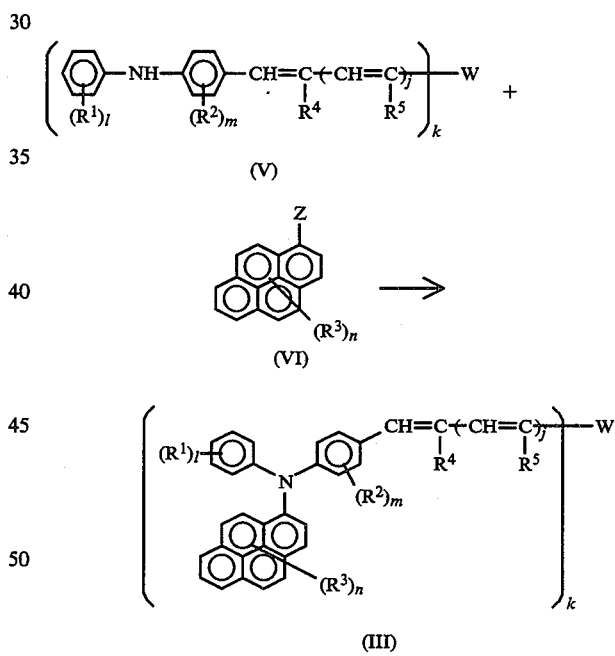

wherein $R^1$, $R^2$, $R^3$, l, m, and n are the same as defined in formula (I); $R^4$, $R^5$, W, j and k are the same as defined in formula (III); and Z represents a halogen atom.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
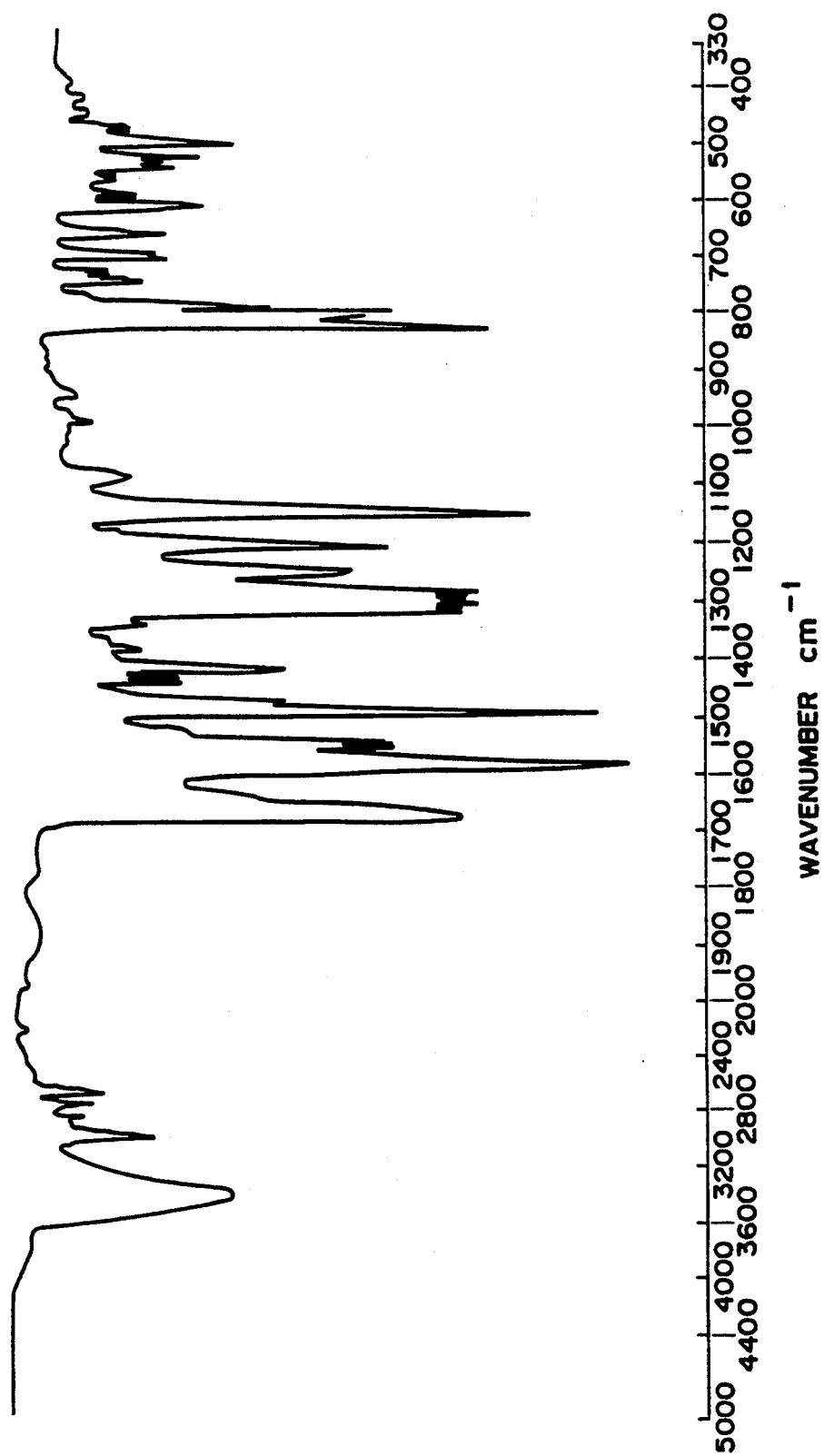
FIG. 1 is an IR absorption spectrum of an aldehyde compound obtained in Example 1 by use of a KBr tablet.

The aldehyde compound with the following formula (I) of the present invention can be used as-an intermediate for producing the pyrenylamine derivative of the present invention:

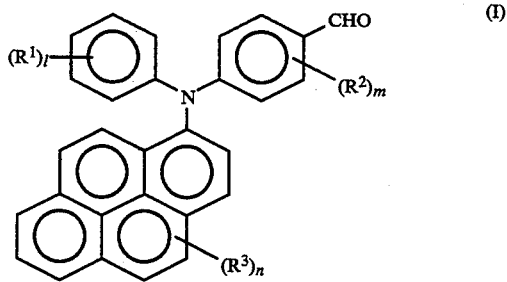

wherein $R^1$ and $R^2$ each represent hydrogen, a halogen atom, nitro group, cyano group, a dialkylamino group, an alkyl group having 1 to 10 carbon atoms, or an alkoxyl group having 1 to 10 carbon atoms; $R^3$ represents hydrogen or an alkyl group having 1 to 10 carbon atoms; l is an integer of 1 to 5; m is an integer of 1 to 4; n is an integer of 1 to 3; and when l, m or n is 2 or more, $R^1$, $R^2$ and $R^3$ may be the same or different.

When $R^1$, $R^2$, or $R^3$ represents an alkyl group in the above-mentioned formula (I), specific examples of the alkyl group are methyl group, ethyl group, propyl group, and butyl group.

When $R^1$ or $R^2$ represents an alkoxyl group in the above-mentioned formula (I), specific examples of the alkoxyl group are methoxy group, ethoxy group, and propoxy group.

The alkyl group or alkoxyl group represented by $R^1$, $R^2$ or $R^3$ in the formula (I) may have a substituent.

Examples of the substituent of the alkyl group represented by $R^1$, $R^2$, $R^3$ in the formula (I) are phenyl group, a halogen atom, an alkoxyl-group having 1 to 4 carbon atoms, and an aryloxy group.

An example of the substituent of the alkoxyl group is a straight-chain or branched-chain alkyl group having 1 to 12 carbon atoms, more preferably a straight-chain or branched-chain alkyl group having 1 to 9 carbon atoms, further preferably a straight-chain or branched-chain alkyl group having 1 to 4 carbon atoms. This straight-chain or branched-chain alkyl group may have a substituent such as a fluorine atom, hydroxyl group, cyano group, an alkoxyl group having 1 to 4 carbon atoms, phenyl group, and a phenyl group having as a substituent a halogen atom, an alkyl group having 1 to 4 carbon atoms and an alkoxyl group having 1 to 4 carbon atoms.

specific examples of the above straight-chain or branched-chain alkyl group are methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group, and 4-phenylbenzyl group.

The phenyl group which is a substituent of the alkyl group represented by $R^1$ or $R^2$ in formula (I) may have a substituent.

Examples of the substituent of the phenyl group represented by $R^1$ or $R^2$ in the formula (I) are an alkyl group such as methyl group, ethyl group, ethoxy group, or propoxy group, an alkoxyl group such as methoxy group, ethoxy group, or propoxy group; and a halogen atom such as bromine, chlorine, or fluorine.

The novel aldehyde compound of formula (I) of the present invention can be produced by subjecting a diphenylaminopyrene compound of formula (II) to formylation in accordance with the following reaction scheme:

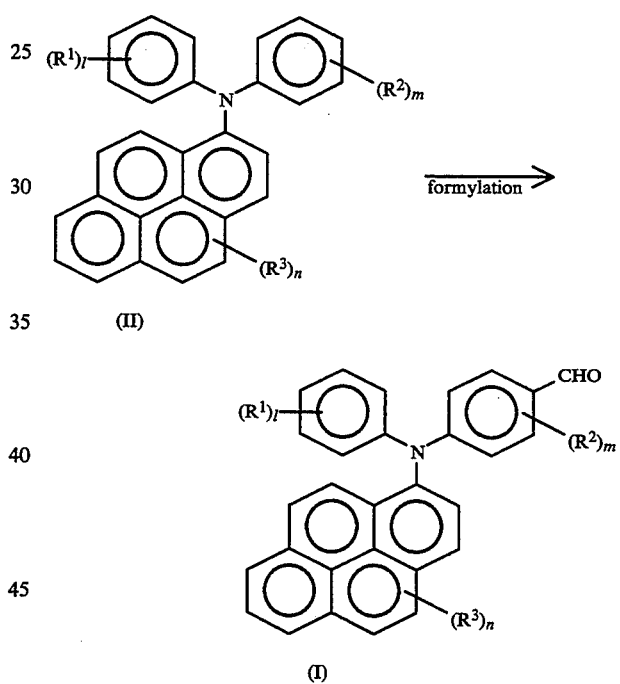

wherein $R^1$, $R^2$, $R^3$, l, m and n-are the same as defined in formula (I).

More specifically, the above aldehyde compound of formula (I) can be produced by allowing the diphenylaminopyrene compound of formula (II) to react with a Vilsmeier reagent to obtain an immonium salt intermediate, and then hydrolyzing the immonium salt intermediate.

The Vilsmeier reagent used in the above reaction can be prepared by use of a conventional method of allowing an amide such as N,N-dimethylformamide or N-methylformanilide to react with an acid halide such as phosphoryl chloride, phosphoryl bromide, oxalyl chloride, phosgene, thionyl chloride, triphenylphosphine - bromine, or hexachlorotriphosphazatriene in an amount equimolar with the amide.

The amount of the Vilsmeier reagent may be a stoichiometric amount with the respect to the diphenylaminopyrene compound of formula (II), but it is preferable that the Vilsmeier reagent be used in an mount more than the equimolar amount with respect to the diphenylaminopyrene compound of formula (II).

The aldehyde compound of formula (I) can be prepared by either of the following two methods according to the present invention:

(i) A method of allowing a Vilsmeier reagent which has already been prepared to react with diphenylaminopyrene compound of formula (II) insolvent, thereby preparing the aldehyde compound; and (ii) A method of adding dropwise the previously mentioned acid halide to a solution containing the diphenylaminopyrene compound of formula (II) and the previously mentioned amide to prepare the Vilsmeier reagent and simultaneously allow the diphenylaminopyrene compound to react with the Vilsmeier reagent, thereby preparing the aldehyde compound.

Examples of the reaction solvent employed in the above-mentioned method are an inert aromatic hydrogen-carbonate such as benzene; chloroform; dichloroethane; and o-dichlorobenzene. In addition, the previously mentioned amides themselves can also be employed as the reaction solvents.

It is preferable that the reaction temperature be in the range of 0 to 150° C., more preferably in the range of 20° to 80° C.

The immonium salt obtained by allowing the diphenylaminopyrene compound of formula (II) to react with the Vilsmeier reagent is hydrolyzed by water or an aqueous alkaline solution, so that the aldehyde compound of formula (I) of the present invention can be derived therefrom.

Examples of the aqueous alkaline solution are an aqueous solution of sodium hydroxide, an aqueous solution of potassium hydroxide, an aqueous solution of sodium acetate, and an aqueous solution of potassium acetate.

The diphenylaminopyrene compound of formula (II) can easily be prepared by use of the method described in Japanese Patent Application 2-321723.

The pyrenylamine derivative having an unsaturated bond of the present invention has the following formula (III):

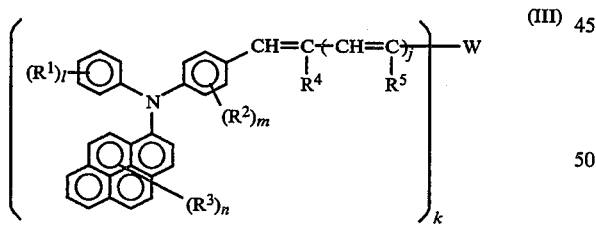

wherein $R^1, R^2, R^3$, l, m, and n are the same as defined in formula (I); $R^4$ and $R^5$ each represent hydrogen, cyano group, formyl group, an alkoxylcarbonyl group, an alkyl group having 1 to 10 carbon atoms, an alkenyl group having 1 to 10 carbon atoms, or phenyl group; w represents hydrogen, an alkyl group having 1 to 10 carbon atoms, a phenylthio group, a bivalent group comprising a chain unsaturated hydrocarbon, a monovalent or bivalent carbocyclic aromatic group, or a monovalent or bivalent group comprising a heterocyclic ring; j is an integer of 0 to 2; k is an inter of 1 or 2; and when l, m or n is 2 or more, $R^1$, $R^2$, or $R^3$ may be the same or different.

When $R^4$ or $R^5$ represents an alkyl group in the above-mentioned formula (III), specific examples of the alkyl group are methyl group, ethyl group, propyl group, and butyl group.

When $R^4$ or $R^5$ represents an alkenyl group in the previously mentioned formula (III), specific examples of the alkenyl group are vinyl group, allyl group, isopropenyl group, butenyl group, pentenyl group, hexenyl group, heptenyl group, octenyl group, and nonenyl group.

The alkyl group, alkenyl group or the phenyl group represented by $R^4$ or $R^5$ in formula (III) may have a substituent.

Examples of the substituent of the alkyl group and alkenyl group are alkoxyl group having 1 to 4 carbon atoms, and a halogen atom.

Examples of the substituent of the phenyl group represented by $R^4$ or $R^5$ in formula (III) are an alkyl group having 1 to 4 carbon atoms, an alkoxyl group having 1 to 4 carbon atoms, an alkylenedioxy group such as methylenedioxy group or ethylenedioxy group, and a halogen atom.

Specific examples of the pyrenylamine derivative having an unsaturated bond of formula (III) according to the present invention are shown in the following Tables 1 to 7:

TABLE 1

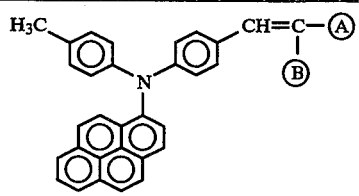

| Compound No. | Ⓐ | Ⓑ |
|---|---|---|
| 1 | —C≡CH | H |
| 2 | —CHO | H |
| 3 | —COOC$_2$H$_5$ | H |
| 4 | —CN | H |
| 5 | —⬡ | H |
| 6 | —CH=CH—⬡ | H |
| 7 | —⬡ | —CH$_3$ |
| 8 | —⬡ | —⬡ |
| 9 | —⬡—CH$_3$ | H |
| 10 | —⬡—C$_2$H$_5$ | H |
| 11 | —⬡—Cl | H |
| 12 | —⬡(C(CH$_3$)$_3$)(OH)(C(CH$_3$)$_3$) | H |

TABLE 1-continued

[Structure: H3C-C6H4-N(pyrenyl)-C6H4-CH=C(A)(B)]

| Compound No. | Ⓐ | Ⓑ |
|---|---|---|
| 13 | -C6H4-OCH3 | H |
| 14 | -C6H4-OC2H5 | H |
| 15 | -C6H4-N(CH3)2 | H |
| 16 | -C6H4-CN | H |
| 17 | -C6H4-NO2 | H |
| 18 | -CH=CH-C6H4-NO2 | H |
| 19 | -S-C6H5 | H |
| 20 | naphthyl | H |
| 21 | anthryl | H |

TABLE 1-continued

[Structure: H3C-C6H4-N(pyrenyl)-C6H4-CH=C(A)(B)]

| Compound No. | Ⓐ | Ⓑ |
|---|---|---|
| 22 | pyrenyl | H |

TABLE 2

[Structure: phenyl-N(pyrenyl)-C6H4-CH=C(C)(D)]

| Compound No. | Ⓒ | Ⓓ |
|---|---|---|
| 23 | phenyl | H |
| 24 | phenyl | —CH3 |
| 25 | phenyl | phenyl |
| 26 | -C6H4-CH3 | phenyl |
| 27 | -C6H4-CH=CH-C6H4-N(phenyl)(pyrenyl) | H |

TABLE 3

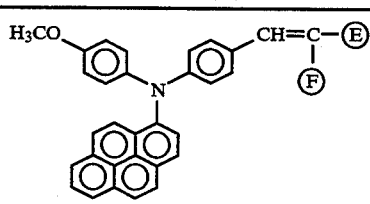

| Compound No. | Ⓔ | Ⓕ |
|---|---|---|
| 28 | phenyl | —H |
| 29 | phenyl | —CH3 |

TABLE 3-continued
| Compound No. | Ⓔ | Ⓕ |
|---|---|---|
| 30 |  | 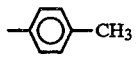 |
| 31 |  | 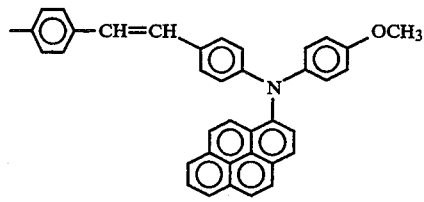 |
| 32 |  | H |
TABLE 4
| Compound No. | Ⓖ | Ⓗ |
|---|---|---|
| 33 |  | —H |
| 34 |  | —CH₃ |
| 35 | 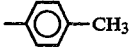 | 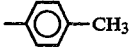 |
| 36 |  |  |
| 37 | 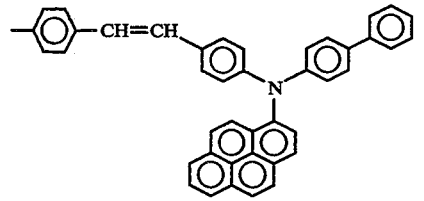 | H |

TABLE 5
| Compound No. | J | K |
|---|---|---|
| 38 |  | —H |
| 39 |  | —CH₃ |
| 40 |  | 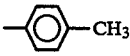 |
| 41 |  | 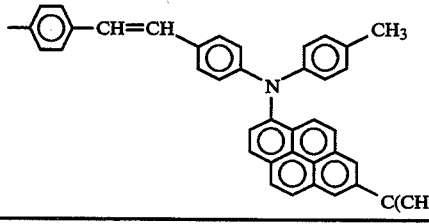 |
| 42 |  | H |
TABLE 6
| Compound No. | L | M |
|---|---|---|
| 43 |  | —H |
| 44 |  | —CH₃ |
| 45 | 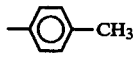 |  |
| 46 | —⬡—CH₃ | —⬡ |

TABLE 6-continued
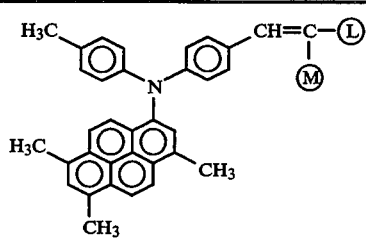
| Compound No. | Ⓛ | Ⓜ |
|---|---|---|
| 47 | (4-methylphenyl)-CH=CH-C₆H₄-N(4-CH₃-C₆H₄)(trimethylpyrene) | H |
TABLE 7
(structure with H₃C-C₆H₄-N(pyrene)-C₆H₄-CH=CH-Ⓝ-CH=CH-C₆H₄-N(pyrene)-C₆H₄-CH₃)
| Compound No. | Ⓝ |
|---|---|
| 48 | —CH=CH— |
| 49 | —C₆H₄— (1,4-phenylene) |
| 50 | (1,2-phenylene) |
| 51 | (1,3-phenylene) |
| 52 | —C₆H₄—CH=CH—C₆H₄— |
| 53 | —C₆H₄—C₆H₄— (biphenyl) |
| 54 | (9,10-anthracenediyl) |
| 55 | (2,5-dimethoxy-1,4-phenylene) |

TABLE 7-continued

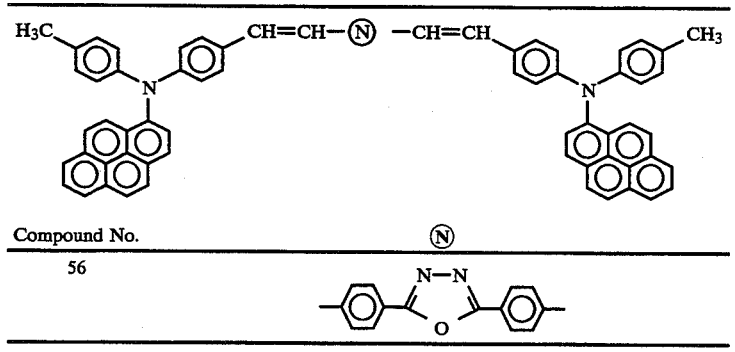

| Compound No. | ⓝ |
|---|---|
| 56 | 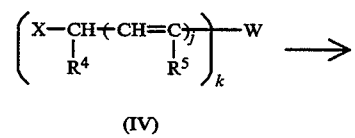 |

The pyrenylamine derivative having an unsaturated bond of formula (III) can be prepared by allowing the previously mentioned aldehyde compound of formula (I) to react with a phosphorus compound of formula (IV) in accordance with the following reaction scheme:

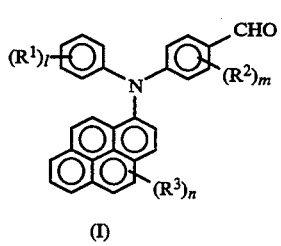

+

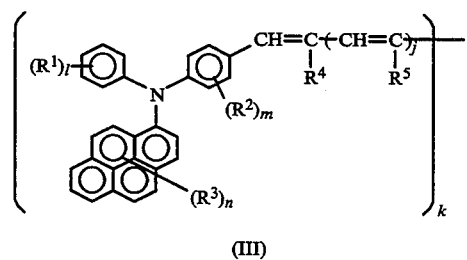

→

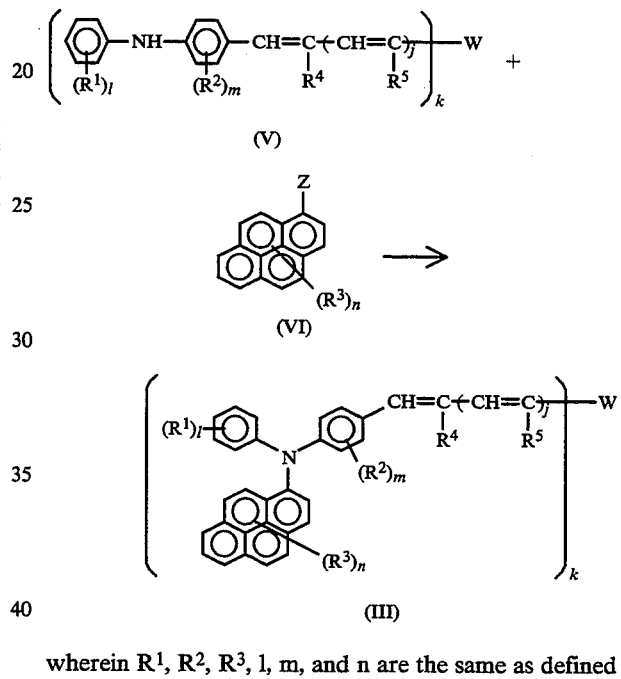

wherein $R^1$, $R^2$, $R^3$, l, m, and n are the same as defined in formula (I); $R^4$ and $R^5$, W, j and k are the same as defined in formula (III); X in formula (IV) represents a phosphonium salt represented by $-P+(R^6)_3Y^-$, or a dialkylphosphite group represented by $-PO(OR^7)_2$, in which $R^6$ represents a phenyl group or an alkyl group having 1 to 10 carbon atoms, Y represents a halogen atom, and $R^7$ represents an alkyl group having 1 to 10 carbon atoms.

The pyrenylamine derivative having an unsaturated bond of formula (III) can also be prepared by allowing a secondary amine compound of formula (V) to react with a pyrene compound of formula (VI) in accordance with the following reaction scheme:

wherein $R^1$, $R^2$, $R^3$, l, m, and n are the same as defined in formula (I); $R^4$ and $R^5$, W, j and k are the same as defined in formula (III); and Z represents a halogen atom.

In the first mentioned method for producing the pyrenylamine derivative having an unsaturated bond of formula (III), the aldehyde compound of formula (I) is allowed to react with a phosphorus compound of formula (IV) in the presence of a basic catalyst at room temperature to about 100° C.

Examples of the basic catalyst for use in the above method are sodium hydroxide, potassium hydroxide, sodium amide, and sodium hydride; and alcoholates such as sodium methylate, and potassium-t-butoxide.

Examples of the reaction solvent for use in the above mentioned method are methanol, ethanol, isopropanol, butanol, 2-methoxyethanol, 1,2-dimethoxyethane, bis(2-methoxyethyl)ether, dioxane, tetrahydrofuran, benzene, toluene, xylene, dimethylsulfoxide, N,N-dimethylformamide, N-methylpyrrolidone, and 1,3-dimethyl-2-imidazolidinone. Of these solvents, polar solvents such as N,N-dimethylformamide and dimethylsulfoxide are preferably employed.

The reaction temperature can be selected from a relatively wide range, depending upon (1) the stabilization of the reaction solvent used in the reaction to the basic catalyst, (2) the condensation reactivities of the compounds of formulas (I) and (IV), and (3) the reactivity of the basic catalyst as a condensation agent in the reaction solvent.

For example, when a polar solvent is employed as the reaction solvent, the reaction temperature can be set in the range of from room temperature to 100° C. in practice, preferably in the range of from room temperature to 80° C. However, in the case where the reaction time is shortened, or a condensation agent with low activity is employed in the reaction, the reaction temperature may be increased.

In the second method for producing the pyrenylamine derivative having an unsaturated bond of formula (III) of the present invention, the secondary amine compound of formula (V) and the pyrene compound of formula (VI) are allowed to react with the addition thereto of copper powder, copper oxide, or copper halogenide and an alkaline material in a sufficient amount to neutralize hydrogen halogenide which is produced in the course of the condensation reaction thereof, in the presence or absence of a reaction solvent in an atmosphere of nitrogen at about 150° to 250° C.

Examples of the alkaline material for use in the above method are sodium hydroxide, potassium hydroxide, sodium carbonate, and potassium carbonate.

Examples of the reaction solvent used in the above reaction are nitrobenzene, dihlorobenzene, quinoline, N,N-dimethylformamide, dimethylsulfoxide, N-methylpyrrolidone, and 1,3-dimethyl-2-imidazolidinone.

The novel dipyrenylamine derivatives having an unsaturated bond of formula (III) of the present invention are remarkably effective as photoconductive materials for use in an electrophotographic photoconductor, and can be optically or chemically sensitized with a sensitizer such as a dye or a Lewis acid. In addition, the above dipyrenylamine derivatives effectively function as charge transporting materials in a function-separating type electrophotographic photoconductor in which an organic or inorganic pigment serves as a charge generating material.

Examples of the sensitizer for use in the present invention are triarylmethane dyes such as Methyl Violet and Crystal Violet; xanthene dyes such as Rose Bengale, Erythrosin, and Rhodamine BJ thiazine dyes such as Methylene Blue; and 2,4,7-trinitro-9-fluorenone, and 2,4-dinitro-9-fluorenone.

Examples of the organic pigment are azo dyes such as C. I. Pigment Blue 25 (C. I. No. 21180), C. I. Pigment Red 41 (C. I. No. 21200), and C. I. Basic Red 3 (C. I. No. 45210); phthalocyanine pigments such as C. I. Pigment Blue 16 (C. I. No. 74100); indigo pigments such as C. I. Vat Brown 5 (C. I. No. 73410), and C. I. Vat Dye (C. I. No.=73030); perylene pigments such as Algol Scarlet B, and Indanthrene Scarlet R.

In addition, examples of the inorganic pigment for use in the present invention are selenium, selenium—tellurium, cadmium sulfide, and s-silicone.

Other features of this invention will become apparent in the course of the following description of exemplary embodiments, which are given for illustration of the invention and are not intended to be limiting thereof.

EXAMPLE 1

Synthesis of N-(4-formylphenyl)-N-(4-methylphenyl)-1-aminopyrene 5.15 g (33.6 mmol) of phosphorus oxychloride was added dropwise to 29.24g (400 mmol) of N,N-dimethylformamide at 0° to 3° C. over a period of 17 minutes under an ice-cooled condition, whereby a Vilsmeier reagent was produced.

To the Vilsmeier reagent thus obtained, 10.74g (28.0 mmol) of N-phenyl-N-(4-methylphenyl)-1-aminopyrene was added. The mixture was warmed to room temperature with stirring over a period of 30 minutes and further stirred at 70° to 75° C. for five hours.

The mixture was then cooled to room temperature and poured into 300 ml of iced water. This mixture was made basic with the addition of an aqueous solution of sodium hydroxide (20 wt. %) and stirred for one hour, whereby a yellow precipitate was obtained.

The yellow precipitate thus obtained was extracted with toluene. The extracting toluene layer was washed with water, and dried over anhydrous magnesium sulfate. Toluene was distilled away from the extracting toluene solution under reduced pressure, whereby an oily orange material was obtained.

The oily material thus obtained was subjected to silica gel column chromatography using toluene as an eluting solvent to obtain a product. The product was recrystallized from a mixed solvent of ethanol and ethyl acetate, so that 9.47g of N-(4-formylphenyl)-N-(4-methylphenyl)-1-aminopyrene was obtained as yellow needle crystals in a yield of 82.2%. The melting point of the above compound was 172.5° to 174.5° C.

The results of the elemental analysis of the above compound were as follows:

|  | % C | % H | % N |
|---|---|---|---|
| Found | 87.66 | 5.06 | 3.40 |
| Calcd. | 87.56 | 5.14 | 3.40 |

The above calculation was based on the formula for N-( 4-formylphenyl ) -N-( 4-methylphenyl ) -1-aminopyrene of $C_{30}H_{21}NO$.

FIG. 1 shows an IR absorption spectrum of the above aldehyde compound taken by use of a KBr tablet.

The IR absorption spectrum indicates the appearance of the characteristic absorption peaks of $\nu$C-H (aldehyde) at 2820 cm$^{-1}$ and 2740 cm$^{-1}$, and the characteristic absorption peak of $\nu_{C=O}$ (aldehyde) at 1680 cm$^{-1}$.

EXAMPLE 2

The procedure for preparation of N-( 4-formylphenyl)-N-(4-methylphenyl)-1-aminopyrene in Example 1 was repeated except that the N,N-dimethylformamide used in Example 1 was replaced by N-methylformanilide, so that an aldehyde compound of the present invention was obtained as shown in Table 8.

Figure 2:
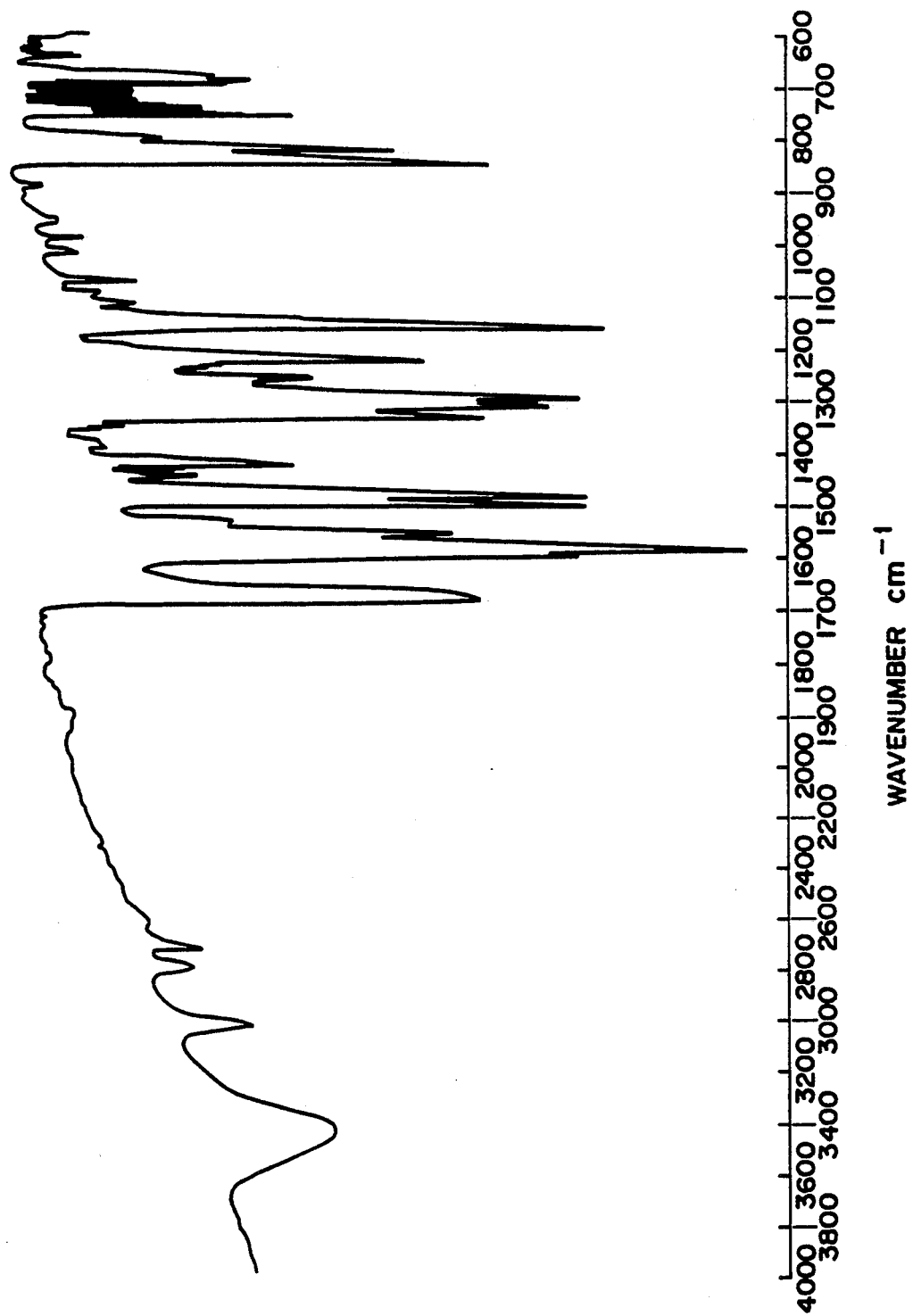
FIG. 2 is an IR absorption spectrum of an aldehyde compound obtained in Example 2 by use of a KBr tablet.

FIG. 2 shows an IR absorption spectrum of the above obtained aldehyde compound taken by use of a KBr tablet.

EXAMPLE 3

The procedure-for preparation of N-(4-formylphenyl)-N-(4-methylphenyl)-1-aminopyrene in Example 1 was repeated except that the N,N-dimethylformamide, and the mixed solvent of ethanol and ethyl acetate used in Example 1 were respectively replaced by N-methylformanilide and a mixed solvent of toluene and ethanol, so that an aldehyde compound of the present invention was obtained as shown in Table 8.

Figure 3:
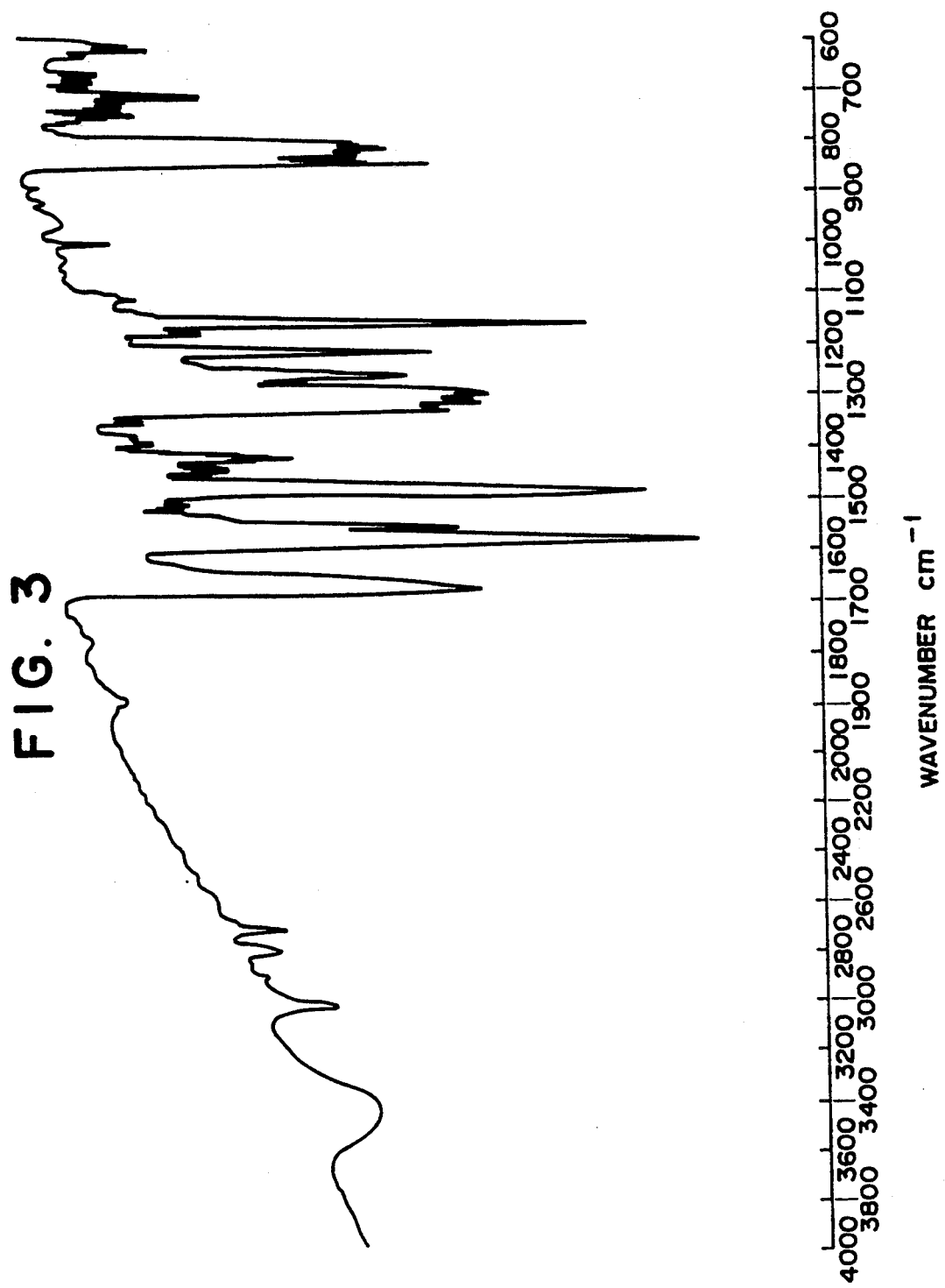
FIG. 3 is an IR absorption spectrum of an aldehyde compound obtained in Example 3 by use of a KBr tablet.

FIG. 3 shows an IR absorption spectrum of the above aldehyde compound taken by use of a KBr tablet.

TABLE 8

| Example No. | Aldehyde Compound | Melting Point (°C.) (Solvent for Recrystallization) | Elemental Analysis Found (Calcd.) | | |
|---|---|---|---|---|---|
| | | | % C | % H | % N |
| 2 | 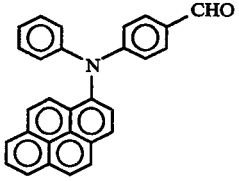 | 149.0–152.0 (Ethyl acetate-ethanol) | 87.86 (87.63) | 5.05 (4.82) | 3.61 (3.52) |
| 3 | 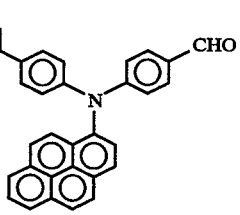 | 185.5–187.5 (Toluene-ethanol) | 88.66 (88.68) | 5.35 (5.17) | 2.75 (2.87) |

EXAMPLE 4

Synthesis of N-(4-methylphenyl)-N-(4-styrylphenyl)-1-aminopyrene (Compound No. 5 in Table 1)

2.47g (6.0 mmol) of the N-(4-formylphenyl)-N-(4-methylphenyl)-1-aminopyrene synthesized in Example 1 and 1.64g (7.2 mmol) of diethyl benzylphosphonate were added to 30 ml of N,N-dimethylformamide. To the mixture thus obtained, 1.39g (7.2 mmol) of a 25% methanol solution sodium methylate was added dropwise over a period of 10 minutes. The above mixture was stirred at room temperature for three hours, poured into 200 ml of iced water, neutralized by the addition of acetic acid, and further stirred for 30 minutes.

A precipitate was formed in the mixture. The precipitate was separated by filtration, washed successively with water and methanol, and dried, so that 2.78g of a crude material was obtained in a yield of 95.2%.

The thus obtained material was subjected to silica gel column chromatography using a mixed solvent of toluene and n-hexane with a volume ratio of 1:3 as an eluting solution. The product was recrystallized from a mixed solvent of ethanol and ethyl acetate, so that 1.87g of N-(4-methylphenyl)-N-(4-styrylphenyl)-1-aminopyrene (Compound No. 5) was obtained as yellow needle crystals in a yield of 64.0%. The melting point of the above compound was 142.8° C. (TG-DTA endothermic peak temperature).

The results of the elemental analysis of the above compound were as follows:

| | % C | % H | % N |
|---|---|---|---|
| Found | 91.62 | 5.56 | 2.82 |
| Calcd. | 91.51 | 5.61 | 2.88 |

The above calculation was based on the formula for N-(4-methylphenyl)-N-(4-styrylphenyl)-1-aminopyrene of $C_{37}H_{27}N$.

Figure 4:
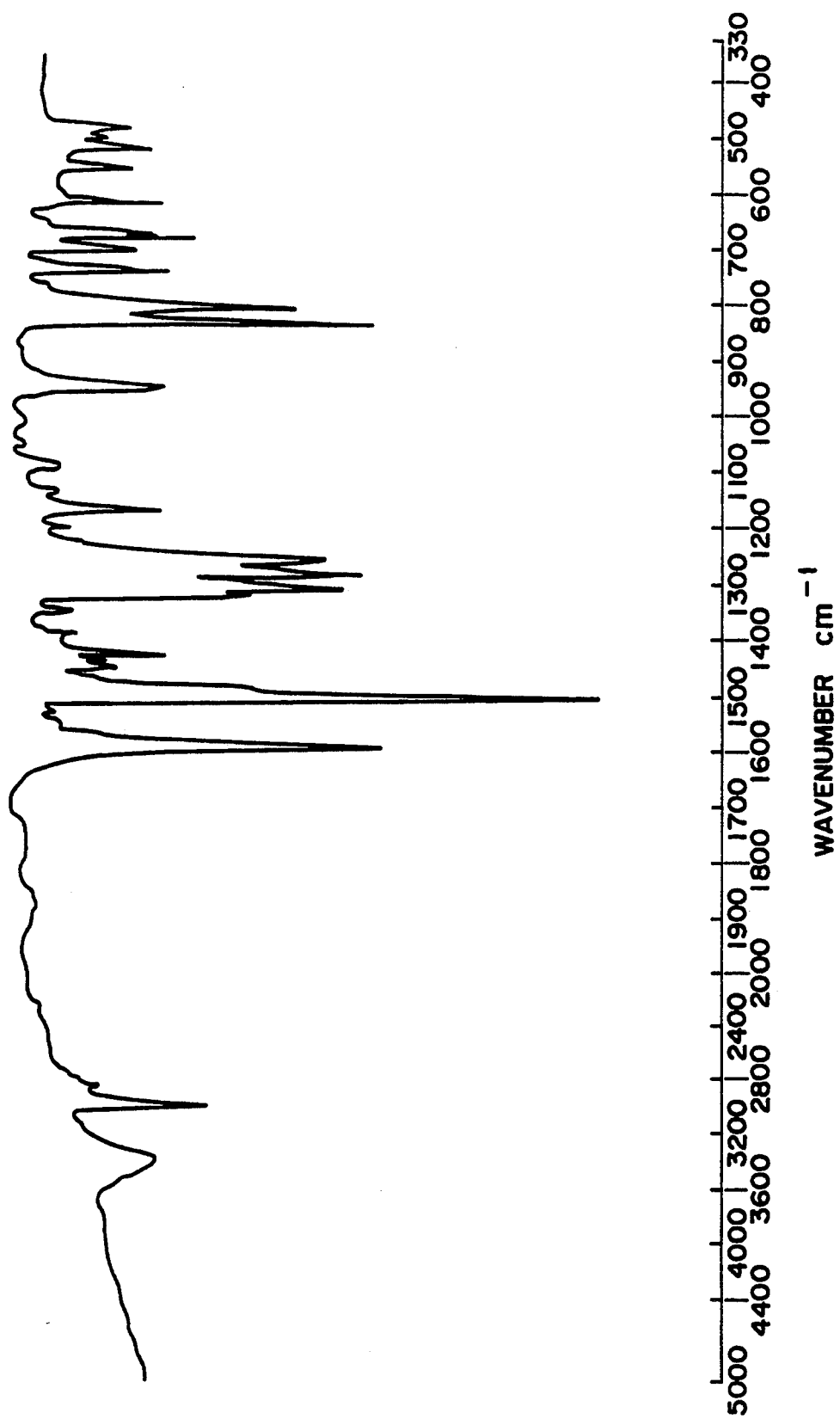
FIG. 4 is an IR absorption spectrum of N-(4-methylphenyl)-N-(4-styrylphenyl)-1-aminopyrene obtained in Example 4 by use of a KBr tablet.

FIG. 4 shows an IR absorption spectrum of the N-(4-methylphenyl)-N-(4-styrylphenyl)-1-aminopyrene taken by use of a KBr tablet.

The IR absorption spectrum of the above obtained compound indicates the appearance of the characteristic absorption peak based on the C-H out-of-plane the deformation vibration of the trans-olefin in the compound at 965 $cm^{-1}$.

EXAMPLE 5

Synthesis of 1,4bis-[N-(1-pyrenyl)-N-(4-methylphenyl)-4-aminostyryl]benzene (Compound No. 49 in Table 7)]

3.30g (8.0 mmol) of the N-(4-formylphenyl)-N-(4-methylphenyl)-1-aminopyrene synthesized in Example 1 and 1.51g (4.0 mmol) of tetraethyl p-xylylenediphosphonate were added to 30 ml of N,N-dimethylformamide. To the mixture thus obtained, 1.86g (9.6 mmol) of a 25% methanol solution of sodium methylate was added dropwise over a period of 25 minutes at room temperature, followed by stirring the mixture at room temperature for ten hours. The above mixture was then poured into 100 ml of methanol, and stirred for 1.5 hours.

A precipitate was formed in the mixture. The precipitate was separated from the mixture by filtration, washed with water twice and with methanol once, and then separated by filtration, so that 2.81g of a crude material was obtained in a yield of 78.7%.

The thus obtained material was subjected to silica gel column chromatography using toluene as an eluting solution. The product was recrystallized successively from N,N-dimethylformamide and a mixed solvent of toluene and dioxane, so that 1,4-bis-[N-(1-pyrenyl)-N-(4-methylphenyl)-4-aminostyryl]benzene (Compound No. 49) was obtained as yellow needle crystals. The melting point of the above compound was 280° C. or more.

The results of the elemental analysis of the above compound were as follows:

| | % C | % H | % N |
|---|---|---|---|
| Found | 91.52 | 5.31 | 3.12 |
| Calcd. | 91.45 | 5.42 | 3.14 |

The above calculation was based on the formula for 1,4-bis-[N-(1-pyrenyl)-N-(4-methylphenyl)-4-aminostyryl]benzene of $C_{68}M_{48}N_2$.

Figure 5:
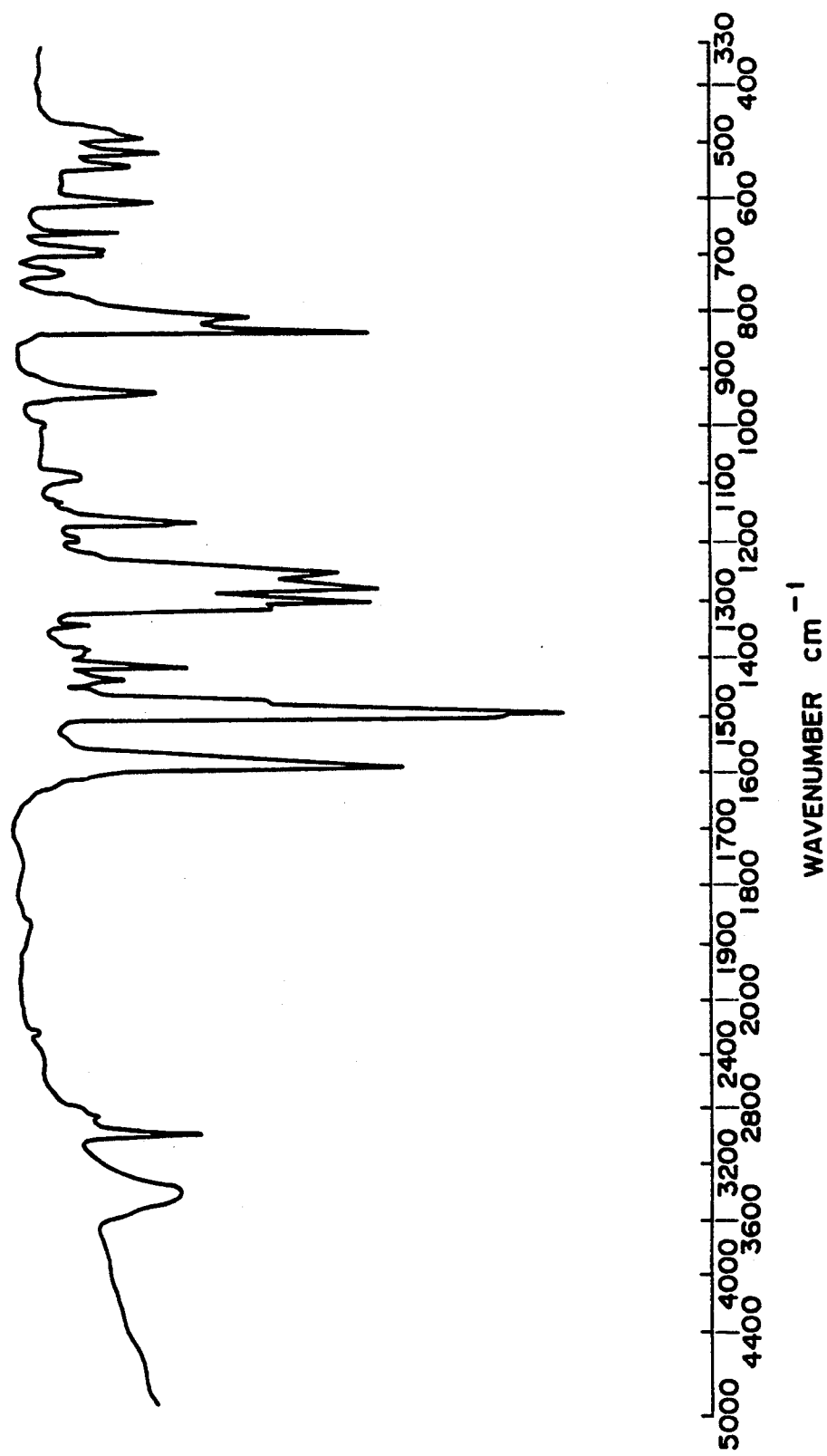
FIG. 5 is an IR absorption spectrum of 1,4-bis-[N-1-pyrenyl-N-(4-methylphenyl)-4-aminostyryl]benzene obtained in Example 5 by use of a KBr tablet.

FIG. 5 shows an IR absorption spectrum of the 1,4-bis-[N-(1-pyrenyl)-N-(4-methylphenyl)-4-aminostyryl]-benzene taken by use of a KBr tablet.

The IR absorption spectrum of the above obtained compound indicates the appearance of the characteristic absorption peak based on the C-H out-of-plane deformation vibration of the trans-olefin in the compound at 960 cm$^{-1}$.

EXAMPLES 6 to 15

The procedure for preparation of N-(4-methylphenyl)-N-(4-styrylphenyl)-1-aminopyrene in Example 4 was repeated except that the diethyl benzylphosphonate used in Example 4 was replaced by the respective phosphorus compounds shown in Table 9, whereby pyrenylamine derivatives having an unsaturated bond of the present invention were obtained as given in Table 9.

TABLE 9

| Ex. No. | Phosphorus Compound | Pyrenylamine Derivative having an unsaturated bond | Melting Point (°C.) (Solvent for Recrystallization) | Elemental Analysis Found (Calcd.) | | |
|---|---|---|---|---|---|---|
| | | | | % C | % H | % N |
| 6 | [structure: (Ph)₂CH—P(O)(OEt)₂] | [structure: H₃C-C₆H₄, pyrenyl-N, C₆H₄-CH=C(Ph)₂] | 177–180.5 (Ethanol-ethyl acetate) | 92.03 (91.94) | 5.49 (5.56) | 2.47 (2.49) |
| 7 | [structure: Ph-CH=CH—CH₂—P(O)(OEt)₂] | [structure: H₃C-C₆H₄, pyrenyl-N, C₆H₄-CH=CH—CH=CH-Ph] | 184.0–187.5 (Ethanol-ethyl acetate) | 91.56 (91.55) | 5.71 (5.71) | 2.74 (2.74) |
| 8 | [structure: H₃C-C₆H₄-CH₂P(O)(OEt)₂] | [structure: H₃C-C₆H₄, pyrenyl-N, C₆H₄-CH=CH-C₆H₄-CH₃] | 169.2–170.3 (Ethyl acetate-ethanol) | 91.09 (91.35) | 6.06 (5.85) | 2.89 (2.80) |
| 9 | [structure: H₃CO-C₆H₄-CH₂P(O)(OEt)₂] | [structure: H₃C-C₆H₄, pyrenyl-N, C₆H₄-CH=CH-C₆H₄-OCH₃] | 180.0–181.0 (Toluene-ethanol) | 88.30 (88.51) | 5.75 (5.67) | 2.76 (2.72) |

TABLE 9-continued
| Ex. No. | Phosphorus Compound | Pyrenylamine Derivative having an unsaturated bond | Melting Point (°C.) (Solvent for Recrystallization) | Elemental Analysis Found (Calcd.) | | |
|---|---|---|---|---|---|---|
| | | | | % C | % H | % N |
| 10 |  |  | 148.0–152.0 (Ethyl acetate-ethanol) | 91.31 (91.35) | 5.95 (5.85) | 2.87 (2.80) |
| 11 | 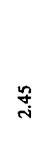 | 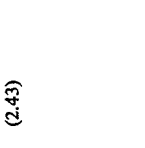 | 175.0–181.5 (Ethyl acetate-ethanol) | 91.71 (91.79) | 5.69 (5.78) | 2.45 (2.43) |
| 12 |  |  | 245.0–246.0 (Toluene-ethanol) | 84.00 (83.75) | 4.82 (4.94) | 5.16 (5.28) |
| 13 |  |  | 150.5–158.0 (Ethyl acetate-ethanol) | 89.00 (88.77) | 5.54 (5.64) | 5.46 (5.60) |

TABLE 9-continued
| Ex. No. | Phosphorus Compound | Pyrenylamine Derivative having an unsaturated bond | Melting Point (°C.) (Solvent for Re-crystallization) | Elemental Analysis Found (Calcd.) | | |
|---|---|---|---|---|---|---|
| | | | | % C | % H | % N |
| 14 | 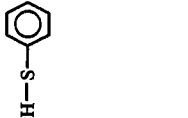 | | 180.0–184.5 (Toluene-ethanol) | 86.01 (85.84) | 5.08 (5.26) | 2.66 (2.71) |
| 15 |  | | 170.0–174.0 (Toluene-ethanol) | 91.11 (90.92) | 5.55 (5.66) | 3.34 (3.42) |

EXAMPLES 16 to 21

The procedure for preparation of N-(4-methylphenyl)-N-(4-styrylphenyl)-1-aminopyrene in Example 4 was repeated except that the N-(4-formylphenyl)-N-(4-methylphenyl)-1-aminopyrene and the diethyl benzylphosphonate used in Example 4 were respectively replaced by the aldehyde compounds and the phosphorus compounds shown in Table 10, whereby pyrenylamine derivatives having an unsaturated bond of the present invention were obtained as given in Table 10.

TABLE 10
| Ex. No. | Aldehyde Compound | Phosphorus Compound | Pyrenylamine Derivative having an unsaturated bond | Melting Point (°C.) (Solvent for Recrystallization) | Elemental Analysis Found (Calcd.) | | |
|---|---|---|---|---|---|---|---|
| | | | | | % C | % H | % N |
| 16 | 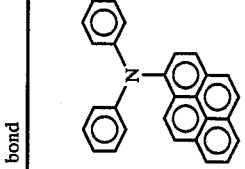 | 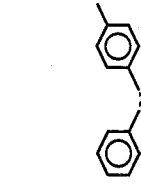 | 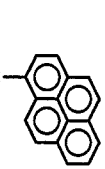 | 154.0–157.0 (Ethyl acetate-ethanol) | 91.32 (91.69) | 5.48 (5.34) | 2.95 (2.97) |
| 17 |  |  |  | 162.0–166.0 (Ethyl acetate-ethanol) | 91.98 (92.10) | 5.40 (5.34) | 2.62 (2.56) |
| 18 | 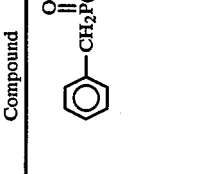 | 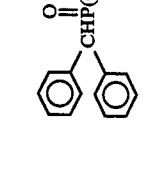 |  | 208.0–213.0 (Toluene-ethanol) | 91.71 (91.71) | 5.60 (5.47) | 2.72 (2.82) |
| 19 | 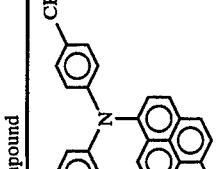 | 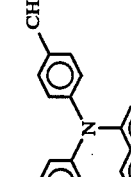 |  | Amorphous | 92.17 (91.94) | 5.23 (5.56) | 2.37 (2.50) |

TABLE 10-continued

| Ex. No. | Aldehyde Compound | Phosphorus Compound | Pyrenylamine Derivative having an unsaturated bond | Melting Point (°C.) (Solvent for Recrystal- lization) | Elemental Analysis Found (Calcd.) | | |
|---|---|---|---|---|---|---|---|
| | | | | | % C | % H | % N |
| 20 | CH=CH—CH₂P(OEt)₂ (with O=) and phenyl | H₃C–C₆H₄– structure | H₃C-Ar-N(pyrenyl)(Ar-CH=CH-CH=CH-Ph) | Amorphous | 91.83 (91.96) | 5.44 (5.66) | 2.22 (2.38) |
| 21 | [(Ph)₃PCH₃]Br | Ar(CHO)-N(pyrenyl)(Ph) | Ar(CH=CH₂)-N(pyrenyl)(Ph) | 157.0–158.0 (Toluene- n-hexane) | 91.29 (91.10) | 5.24 (5.36) | 3.47 (3.54) |

EXAMPLE 22

The procedure for preparation of 1,4-bis-[N-(1-pyrenyl)-N-(4-methylphenyl)-4-aminostyryl]benzene in Example 5 was repeated except that the N-(4-formyl-phenyl)-N-(4-methylphenyl)-1-aminopyrene and tetraethyl p-xylylene-diphosphonate used in Example 5 were respectively replaced by the aldehyde compound and the phosphorus compound shown in the following reaction scheme, whereby a pyrenylamine derivative having an unsaturated bond of the present invention was obtained:

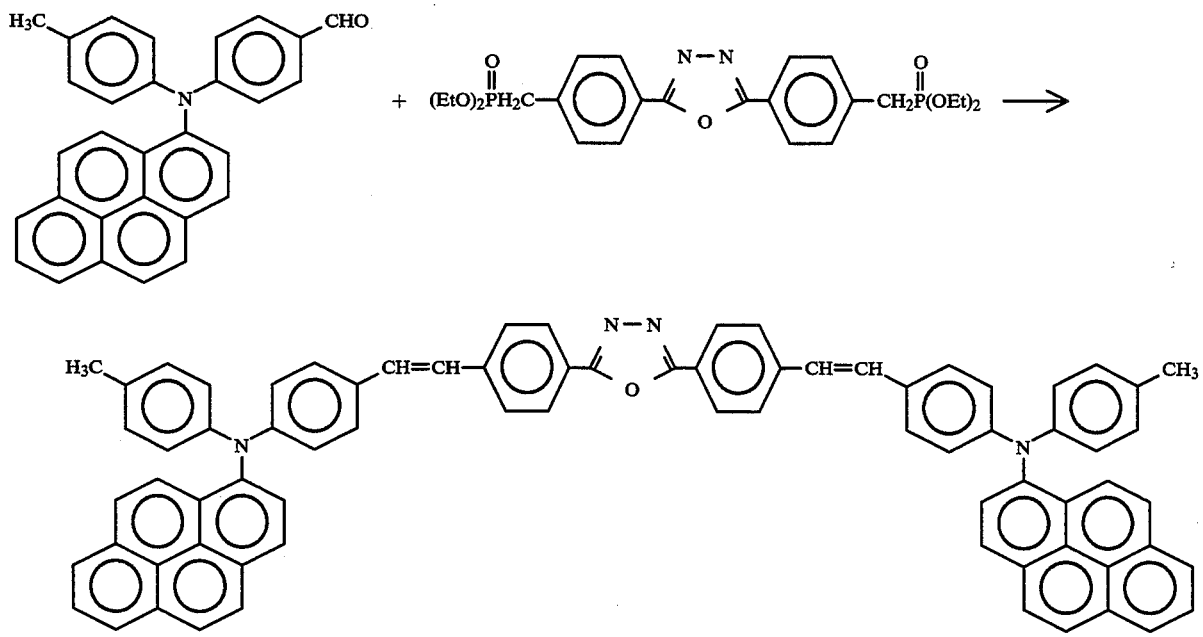

The melting point of the above compound which was recrystallized from toluene was 250.0° C. or more.

The results of the elemental analysis of the above compound were as follows:

|  | % C | % H | % N |
|---|---|---|---|
| Found | 88.24 | 4.96 | 5.29 |
| Calcd. | 88.00 | 5.05 | 5.40 |

EXAMPLE 23

Synthesis of N-(4-methoxyphenyl)-N-(4-styrylphenyl)-1-aminopyrene (Compound No. 28 in Table 3)

0.82g (2.7 mmol) of 4-(4-methoxyphenyl)aminostilbene, 1.34g (4.1 mmol) of 1-iodopyrene, 0.56g (4.1 mmol) of potassium carbonate and 0.10g of copper powder were added to 20 ml of nitrobenzene. The above mixture was refluxed for 15 hours while azeotropic dehydration was being carried out under a stream of nitrogen.

After the mixture was cooled to room temperature, the resulting insoluble material in the mixture was removed therefrom by filtration. The solvent was distilled away from the resulting mixture under reduced pressure with the application of heat thereto. The residue thus obtained was dissolved in toluene, washed with water, and dried over magnesium sulfate. The solvent was distilled away from the mixture under reduced pressure with the application o heat thereto so that an oily dark brown material was obtained.

The oily material thus obtained was subjected to column chromatograph using silica gel as a carrier and a mixed solvent of toluene and n-hexane with a volume ratio of as an eluting solution to obtain a product. The product was recrystallized from a mixed solvent of ethyl acetate and ethanol, so that 0.98g of N-(4-methoxyphenyl)-N-(4-styrylphenyl)-1-aminopyrene (Compound No. 28) was obtained in a yield of 72.6%.

The melting point of the above compound was 145.2° C. (TG-DTA endothermic peak temperature).

The result of the elemental analysis of the compound were as follows:

|  | % C | % H | % N |
|---|---|---|---|
| Found | 88.39 | 5.38 | 2.81 |
| Calcd. | 88.58 | 5.44 | 2.79 |

The above calculation was based on the formula for N-(4-methoxyphenyl)-N-(4-styrylphenyl)-1-aminopyrene of $C_{37}H_{27}NO$.

EXAMPLE 24

Synthesis of N-(4-methoxyphenyl)-N-(4-S-phenylstyryl-phenyl)-1-aminopyrene (Compound No. 30 in Table 3)

The procedure for preparation of N-(4-methoxyphenyl)-N-(4-styrylphenyl)-1-aminopyrene in Example 23 was repeated except that the 4-(4-methoxyphenyl)aminostilbene used in Example 23 was replaced by 4'-(4-methoxyphenyl)-amino-α-phenylstilbene, so that N-(4-methoxyphenyl)-N-(4-β-phenylstyrylphenyl)-1-aminopyrene (Compound No. 30) was obtained.

The melting point of the above compound was 183.2° C. (TG-DTA endothermic peak temperature).

The results of the elemental analysis of the compound were as follows:

| | % C | % H | % N |
|---|---|---|---|
| Found | 89.48 | 5.41 | 2.39 |
| Calcd. | 89.39 | 5.42 | 2.42 |

The above calculation was based on the formula for N-(4-methoxyphenyl)-N-(4-β-phenylstyrylphenyl)-1-aminopyrene of $C_{43}H_{31}NO$.

The pyrenylamine derivatives having an unsaturated bond of formula (III) are useful as organic photoconductive materials and fluorescent whitening agents for use in electrophotographic photoconductors. In particular, when the pyrenylamine derivatives of the present invention are employed as the organic photoconductive materials for use in electrophotographic photoconductors, the fundamental characteristics necessary for the photoconductors can be satisfied and photoconductors having flexibility can also be provided.

What is claimed is:

1. An aldehyde compound of formula (I):

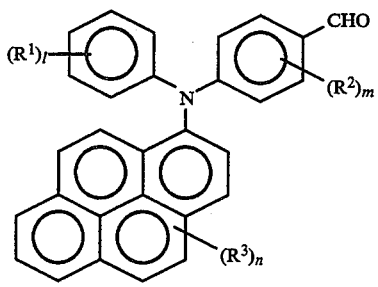

(I)

wherein $R^1$ and $R^2$ each represent hydrogen, a halogen atom, nitro group, cyano group, a dialkylamino group, a substituted or unsubstituted alkyl group having 1 to 10 carbon atoms, a substituted or unsubstituted alkoxy group having 1 to 10 carbon atoms, or a substituted or unsubstituted phenyl group; $R^3$ represents hydrogen or substituted or unsubstituted alkyl group having 1 to 10 carbon atoms, l is an integer of 1 to 5; m is an integer of 1 to 4; n is an integer of 1 to 3; and when l, m or n is 2 or more, $R^1$, $R^2$ and $R^3$ may be the same or different.

2. The aldehyde compound as claimed in claim 1, wherein said substituted alkyl group represented by $R^1$, $R^2$, or $R^3$ has a substituent selected from the group consisting of a phenyl group, a halogen atom, an alkoxyl group having 1 to 4 carbon atoms, and an aryloxy group.

3. The aldehyde compound as claimed in claim 1, wherein said substituted alkyl group represented by $R^1$ or $R^2$ has a substituent a substituted or unsubstituted straight chain or branched chain alkyl group having 1 to 12 carbon atoms.

4. The aldehyde compound as claimed in claim 1, wherein at least one of $R^1$, $R^2$, and $R^3$ represents an alkyl group selected from the group consisting of methyl, ethyl, propyl, and butyl.

5. The aldehyde compound as claimed in claim 1, wherein at least one of $R^1$ and $R^2$ represents an alkoxyl group selected from the group consisting of methoxy, ethoxy, and propoxy.

6. The aldehyde compound as claimed in claim 3, wherein at least one of $R^1$ and $R^2$ is a substituted or unsubstituted straight chain or branched chain alkyl group having 1 to 9 carbon atoms.

7. The aldehyde compound as claimed in claim 6, wherein said substituted or unsubstituted straight chain or branched chain alkyl group has from 1 to 4 carbon atoms.

8. The aldehyde compound as claimed in claim 3, wherein at least one of $R^1$ and $R_2$ is a substituted straight chain or branched chain alkyl group having a substituent selected from the group consisting of fluorine, hydroxyl, cyano, $C_1$–$C_4$ alkoxyl, unsubstituted phenyl, and substituted phenyl having as a substituent a group selected from a halogen, an $C_1$–$C_4$ alkyl, and a $C_1$–$C_4$ alkoxy.

9. The aldehyde compound as claimed in claim 1, wherein said substituted phenyl group represented by $R^1$ or $R^2$ has a substituent selected from the group consisting of methyl, ethyl, methoxy, ethoxy, propoxy, bromine, chlorine, or fluorine.

* * * * *

UNITED STATES PATENT AND TRADEMARK OFFICE
CERTIFICATE OF CORRECTION

PATENT NO. : 5,344,985

DATED : SEPTEMBER 6, 1994

INVENTOR(S) : CHIAKI TANAKA ET AL

It is certified that error appears in the above-identified patent and that said Letters Patent is hereby corrected as shown below:

In the Abstract, line 5, after "m, n", insert --,--;

line 6, after "defined", insert --in--.

Column 3, line 42, delete "inter" and insert --integer--.

Column 5, line 67, delete "specific" and insert --Specific---.

Column 7, line 2, delete "mount" and insert --amount--;

line 64, delete "inter" and insert --integer--.

Column 19, line 44, delete "BJ" and insert --B;--;

line 53, after "C.I. No." delete "=";

line 57, delete "s-silicone" and insert

--$\alpha$-silicone--.

UNITED STATES PATENT AND TRADEMARK OFFICE
CERTIFICATE OF CORRECTION

PATENT NO. : 5,344,985

DATED : SEPTEMBER 6, 1994

INVENTOR(S) : CHIAKI TANAKA ET AL

It is certified that error appears in the above-identified patent and that said Letters Patent is hereby corrected as shown below:

Column 22, line 68, delete "$C_{68}M_{48}N_2$" and insert --$C_{68}H_{48}N_2$--.

Column 38, line 1, after "application", delete "o" and insert --of--;

line 55, delete "N-(4-S-phenylstyryl", and insert --N-(4-$\beta$-phenylstyryl--.

Column 40, line 10, delete "alkyl" and insert --alkoxy--.

Signed and Sealed this

Seventh Day of November, 1995

Attest:

BRUCE LEHMAN

*Attesting Officer*  *Commissioner of Patents and Trademarks*